United States Patent
Chen et al.

(10) Patent No.: US 12,060,356 B2
(45) Date of Patent: Aug. 13, 2024

(54) 7 (METHYLAMINO)PYRAZOLO[1,5-A]PYRIMIDINE-3-CARBOXAMIDE DERIVATIVES

(71) Applicant: Eli Lilly and Company, Indianapolis, IN (US)

(72) Inventors: Zhaogen Chen, Carmel, IN (US); Theodore Curtis Jessop, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 695 days.

(21) Appl. No.: 17/311,406

(22) PCT Filed: Dec. 4, 2019

(86) PCT No.: PCT/US2019/064427
§ 371 (c)(1),
(2) Date: Jun. 7, 2021

(87) PCT Pub. No.: WO2020/123225
PCT Pub. Date: Jun. 18, 2020

(65) Prior Publication Data
US 2022/0024933 A1    Jan. 27, 2022

Related U.S. Application Data

(60) Provisional application No. 62/777,395, filed on Dec. 10, 2018.

(51) Int. Cl.
*C07D 487/04*    (2006.01)

(52) U.S. Cl.
CPC .................. *C07D 487/04* (2013.01)

(58) Field of Classification Search
CPC .................................................. C07D 487/04
See application file for complete search history.

(56) References Cited

U.S. PATENT DOCUMENTS

| | | |
|---|---|---|
| 7,557,110 B2 | 7/2009 | Kenichiro et al. |
| 7,645,762 B2 | 1/2010 | Paruch et al. |
| 8,637,526 B2 | 1/2014 | Blaney et al. |
| 8,921,380 B2 | 12/2014 | Tanimoto et al. |
| 10,273,237 B2 | 4/2019 | Liu et al. |
| 11,634,423 B2 * | 4/2023 | Bleisch .................. A61P 17/06 514/259.3 |
| 11,891,400 B2 * | 2/2024 | Chen .................... C07D 487/04 |
| 2006/0089499 A1 | 4/2006 | Gebauer et al. |
| 2016/0304524 A1 | 10/2016 | Liu et al. |
| 2018/0325899 A1 | 11/2018 | Weinstein et al. |
| 2019/0225620 A1 | 7/2019 | Spergel et al. |

FOREIGN PATENT DOCUMENTS

| | | |
|---|---|---|
| WO | 2004/022561 A1 | 3/2004 |
| WO | 2004/026229 A2 | 4/2004 |
| WO | 2005/077954 A2 | 8/2005 |
| WO | 2010/051549 A1 | 5/2010 |
| WO | 2012/078855 A1 | 6/2012 |
| WO | 2017/087590 A1 | 5/2017 |
| WO | 2018/093968 A1 | 5/2018 |
| WO | 2019/023468 A1 | 1/2019 |
| WO | 2020/055636 A1 | 3/2020 |
| WO | 2020/081508 A1 | 4/2020 |

OTHER PUBLICATIONS

Marroqui, L., et al., Diabetes, vol. 64, pp. 3808-3817 (2015).
Moslin, R., et al., MedChemComm vol. (4), pp. 700-712 (2017).
U.S. Appl. No. 17/168,399, filed Feb. 5, 2021 (unpublished).
Novinson, et al, "Synthesis of Antifungal Properties of Certain 7-Alkylaminopyrazolo[1,5-a]pyrimidines," J Med Chem, vol. 20(2), pp. 296-299 (1977).
Shiota, et al., "Synthesis and Structure-Activity Relationship of a New Series of Potent Angiotensin II Receptor Antagonists: Pyrazolo[1,5-a]pyrimidine Derivatives," Chem Pharm Bull, vol. 47(7), pp. 928-938 (1999).

* cited by examiner

*Primary Examiner* — Nizal S Chandrakumar
(74) *Attorney, Agent, or Firm* — Robert D. Shereda

(57) ABSTRACT

The present invention provides a compound of Formula (I) wherein R is (II) or (III); or a pharmaceutically acceptable salt thereof, useful for treating psoriasis or systemic lupus erythematosus.

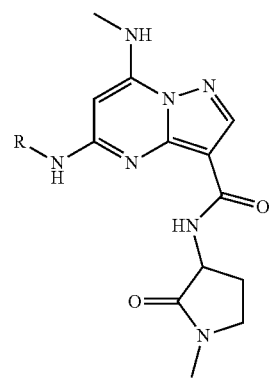

(I)

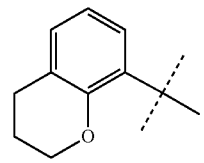

(II)

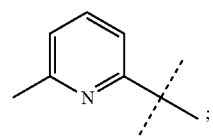

(III)

11 Claims, No Drawings

7 (METHYLAMINO)PYRAZOLO[1,5-A] PYRIMIDINE-3-CARBOXAMIDE DERIVATIVES

The present invention relates to certain novel compounds that bind to the pseudokinase domain (JH2) of TYK2 and inhibit certain cytokine signaling, in particular IL-23 and IFNα signaling, to pharmaceutical compositions comprising the compounds, to methods of using the compounds to treat certain autoimmune diseases, such as psoriasis, and to intermediates and processes useful in the synthesis of the compounds.

The present invention is in the field of treatment of psoriasis and/or other autoimmune diseases, such as diabetes, thought to be mediated by TYK2 signaling of certain proinflammatory cytokines (See e.g., J. S. Tokarski, et al., *J. Biol. Chem.*, vol. 290(17), pages 11061-11074 (2015); and, L. Marroqui, et al., *Diabetes*, vol. 64, pages 3808-3817 (2015)). Psoriasis is a chronic skin disease, which is estimated to affect approximately 2% of the general population. Treatment options for psoriasis include, for example, topical treatments, such as corticosteroids, phototherapy, such as ultraviolet B (UVB) light, and systemic treatments, such as methotrexate and apremilast. Unfortunately, such agents do not always provide effective treatment and can be associated with various untoward side effects. Thus, there is an unmet need in the treatment of autoimmune diseases, such as psoriasis, systemic lupus erythematosus (SLE), and diabetes, and new treatment options are desired.

WO 2017/087590 discloses certain imidazopyridazine compounds useful for the treatment of autoimmune conditions, such as psoriasis or SLE, through modulation of IL-12, IL-23, and/or IFNα by acting on TYK2 to cause signal transduction inhibition. U.S. Pat. No. 7,557,110 discloses certain pyrazolo[1,5-a]pyrimidine derivatives as kinase inhibitors useful for treating kinase mediated disorders, such as inflammatory disease and autoimmune disease. Certain imidazo[1,2-b]pyridazine TYK2 pseudokinase ligands are disclosed by R. Moslin, et al., *Med. Chem. Commun.*, vol. 8, pages 700-712 (2017) as potent and selective inhibitors of TYK2 signaling.

Additional compounds that act on the TYK2 JH2 domain and inhibit signal transduction of IL-23 and IFNα are desired. The present invention provides certain novel compounds that bind to the TYK2 JH2 domain. In addition, the present invention provides certain novel compounds that inhibit IL-23 and IFNα signaling. Thus, the present invention provides certain novel compounds that are useful for treating autoimmune diseases, such as psoriasis and SLE.

Accordingly, the present invention provides a compound of Formula I.

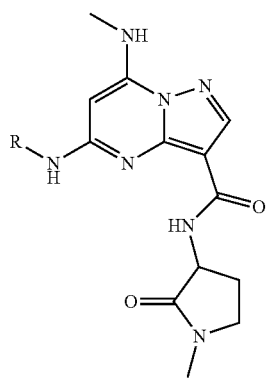

Formula I wherein R is

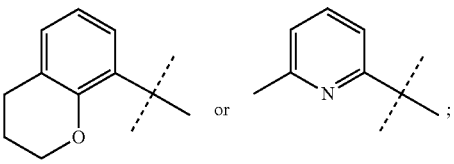

or a pharmaceutically acceptable salt thereof.

The present invention also provides a method of treating psoriasis in a patient in need of such treatment, comprising administering to the patient an effective amount of a compound of Formula I, or a pharmaceutically acceptable salt thereof. The present invention further provides a method of treating SLE in a patient in need of such treatment, comprising administering to the patient an effective amount of a compound of Formula I, or a pharmaceutically acceptable salt thereof. The present invention further provides a method of treating a disease selected from the group consisting of inflammatory bowel disease, ulcerative colitis, Crohn's Disease, psoriatic arthritis, rheumatoid arthritis (RA), alopecia areata, atopic dermatitis, axial spondyloarthritis, multiple sclerosis (MS), type 1 diabetes, type 2 diabetes, and latent autoimmune diabetes of adults (LADA) in a patient in need of such treatment, comprising administering to the patient an effective amount of a compound of Formula I, or a pharmaceutically acceptable salt thereof. Furthermore, this invention provides a compound of Formula I, or a pharmaceutically acceptable salt thereof for use in therapy, in particular for use in treating psoriasis. In addition, this invention provides a compound of Formula I, or a pharmaceutically acceptable salt thereof, for use in treating SLE. The invention also provides a compound of Formula I, or a pharmaceutically acceptable salt thereof, for use in treating a disease selected from the group consisting of inflammatory bowel disease, ulcerative colitis, Crohn's Disease, psoriatic arthritis, RA, alopecia areata, atopic dermatitis, axial spondyloarthritis, MS, type 1 diabetes, type 2 diabetes, and latent autoimmune diabetes of adults (LADA).

This invention also provides the use of a compound of Formula I, or a pharmaceutically acceptable salt thereof, for the manufacture of a medicament for treating psoriasis. In addition, this invention provides the use of a compound of Formula I, or a pharmaceutically acceptable salt thereof, for the manufacture of a medicament for treating SLE. The invention also provides the use of a compound of Formula I, or a pharmaceutically acceptable salt thereof, for the manufacture of a medicament for treating a disease selected from the group consisting of inflammatory bowel disease, ulcerative colitis, Crohn's Disease, psoriatic arthritis, RA, alopecia areata, atopic dermatitis, axial spondyloarthritis, MS, type 1 diabetes, type 2 diabetes, and latent autoimmune diabetes of adults (LADA).

The invention further provides a pharmaceutical composition, comprising a compound of Formula I, or a pharmaceutically acceptable salt thereof, with one or more pharmaceutically acceptable carriers, diluents, or excipients. The invention further provides a process for preparing a pharmaceutical composition, comprising admixing a compound of Formula I, or a pharmaceutically acceptable salt thereof, with one or more pharmaceutically acceptable carriers, diluents, or excipients. This invention also encompasses novel intermediates and processes for the synthesis of the compounds of Formula I.

As used herein, the terms "treating", "treatment", or "to treat" includes restraining, slowing, stopping, or reversing the progression or severity of an existing symptom or disorder.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are formulated as pharmaceutical compositions administered by any route which makes the compound bioavailable. Most preferably, such compositions are for oral administration. Such pharmaceutical compositions and processes for preparing same are well known in the art (See, e.g., Remington: The Science and Practice of Pharmacy, L. V. Allen, Editor, $22^{nd}$ Edition, Pharmaceutical Press, 2012).

The compound of Formula I, or a pharmaceutically acceptable salt thereof, is particularly useful in the treatment methods of the invention, with all configurations, including enantiomers, and mixtures thereof, including racemates, being contemplated within the scope of the invention. It will be understood that these configurations are applicable both to the treatment methods and to the compounds of the invention.

Compounds of the present invention include:

Formula Ia

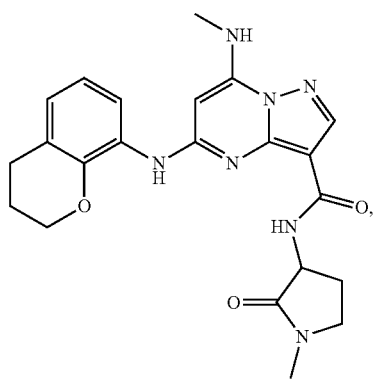

Formula Ia(i)

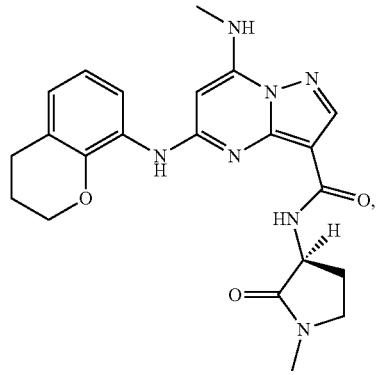

Formula Ia(ii)

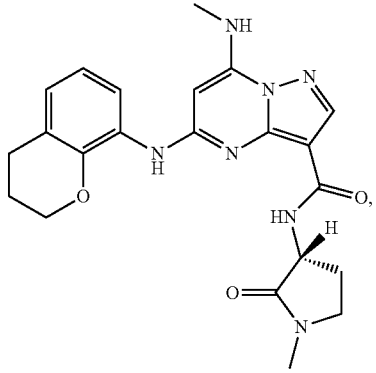

Formula Ib

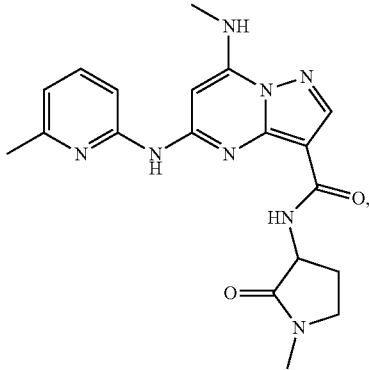

Formula Ib(i)

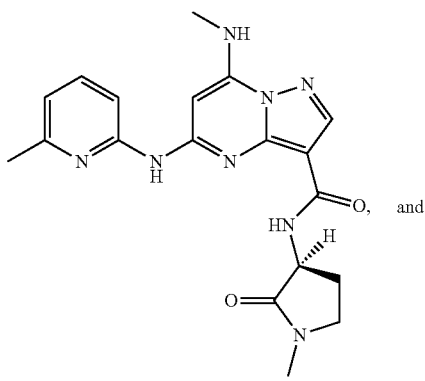

and

-continued

Formula Ib(ii)

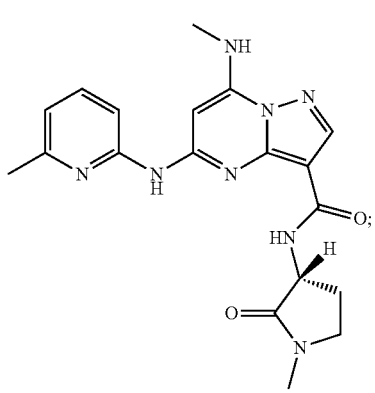

and the pharmaceutically acceptable salts thereof.

The compounds of Formula Ia(ii) and Formula Ib(ii) are preferred, with the compound of Formula Ia(ii) and the pharmaceutically acceptable salts thereof being particularly preferred.

Certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Individual isomers, including enantiomers, may be separated or resolved by one of ordinary skill in the art at any convenient point in the synthesis of compounds of the invention, by methods such as selective crystallization techniques or chiral chromatography (See, for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

A pharmaceutically acceptable salt of a compound of the invention can be formed, for example, by reaction of an appropriate free base of a compound of the invention, an appropriate pharmaceutically acceptable acid in a suitable solvent such as diethyl ether under standard conditions well known in the art. Additionally, the formation of such pharmaceutically acceptable salts can occur simultaneously upon deprotection of a nitrogen protecting group. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Certain abbreviations are defined as follows: "BINAP" refers to (±)-2,2'-Bis(diphenylphosphino)-1,1'-binaphthalene; "BOP" refers to (Benzotriazol-1-yloxy)tris(dimethylamino)phosphonium hexafluorophosphate; "BrettPhos" refers to dicyclohexyl[3,6-dimethoxy-2',4',6'-tris(1-methylethyl)[1,1'-biphenyl]-2-yl]phosphine; "t-BuOH" refers to t-butanol and t-butyl alcohol; "BSA" refers to Bovine Serum Albumin; "CDI" refers 1,1'-carbonyldiimidazole; "DCC" refers to 1,3-dicyclohexylcarbodiimide; "DCE" refers to dichloroethane; "DCM" refers to dichloromethane; "DEM" refers to diethylmalonate; "DIC" refers to 1,3-diisopropylcarbodiimide; "DIEA" refers to N,N-diisopropylethylamine; "DMAP" refers to dimethylaminopyridine; "DMEM" refers to Dulbecco's Modified Eagle's Medium; "DMF" refers to N,N-dimethylformamide; "DMSO" refers to dimethyl sulfoxide; "DPPA" refers to diphenylphosphoryl azide; "EDCI" refers to 1-(3-dimethylaminopropyl)-3-ethylcarbodiimide hydrochloride; "EtOAc" refers to ethyl acetate; "EtOH" refers to ethanol and ethyl alcohol; "FBS" refers to Fetal Bovine Serum; "Grubbs catalyst $2^{nd}$ generation" refers to (1,3-Bis(2,4,6-trimethylphenyl)-2-imidazolidinylidene) dichloro(phenylmethylene)(tricyclohexylphosphine)ruthenium; "HATU" refers to 1-[bis(dimethylamino)methylene]-1H-1,2,3-triazolo[4,5-b]pyridinium 3-oxid hexafluorophosphate; "HBTU" refers to (1H-benzotriazol-1-yloxy)(dimethylamino)-N,N-dimethylmethaniminium hexafluorophosphate; "HEPES" refers to 4-(2-hydroxyethyl)-1-piperazineethanesulfonic acid; "HOAt" refers to 1-hydroxy-7-azobenzotriazole; "HOBt" refers to 1-hydroxylbenzotriazole hydrate; "HPLC" refers to high-performance liquid chromatography; "IFNα" refers to interferon alpha; "IL-12" refers to interleukin 12; "IL-23" refers to interleukin 23; "IPA" refers to isopropanol and isopropyl alcohol; "JAK" refers to Janus kinase; "LiHMDS" refers to lithium hexamethyldisilazide; "MeI" refers to methyl iodide; "MeNH$_2$" refers to methylamine; "MeOH" refers to methanol and methyl alcohol; "MTBE" refers to methyl tert-butyl ether; "NaOEt" refers to sodium ethoxide; "Ni NTA" refers to nickel-nitrilotriacetic acid; "PBS" refers to Phosphate Buffered Saline; "Pd(dppf)Cl$_2$" refers to (1,1'-bis(diphenylphosphino)ferrocene)palladium(II) dichloride; "Pd(OAc)$_2$" refers to palladium (II) acetate; "PyBOP" refers to (benzotriazol-1-yl-oxytripyrrolidinophosphonium hexafluorophosphate); "PyBrOP" refers to bromo(tri-pyrrolidinyl)phosphoniumhexafluorophosphate; "RPM" refers to revolutions per minute; "RPMI" refers to Roswell Park Memorial Institute; "SPA" refers to scintillation proximity assay; "TEA" refers to triethylamine; "TFA" refers to trifluoroacetic acid; "THF" refers to tetrahydrofuran; "TYK2" refers to tyrosine kinase 2; "UVB" refers to ultraviolet B; "STAT" refers to signal transducer and activator of transcription protein; and "YSI" refers to yttrium silicate.

The compounds of the present invention, or pharmaceutically acceptable salts thereof, may be prepared by a variety of procedures known to one of ordinary skill in the art, some of which are illustrated in the schemes, preparations, and examples below. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention.

Scheme 1

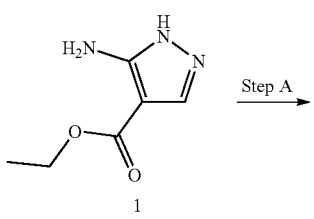

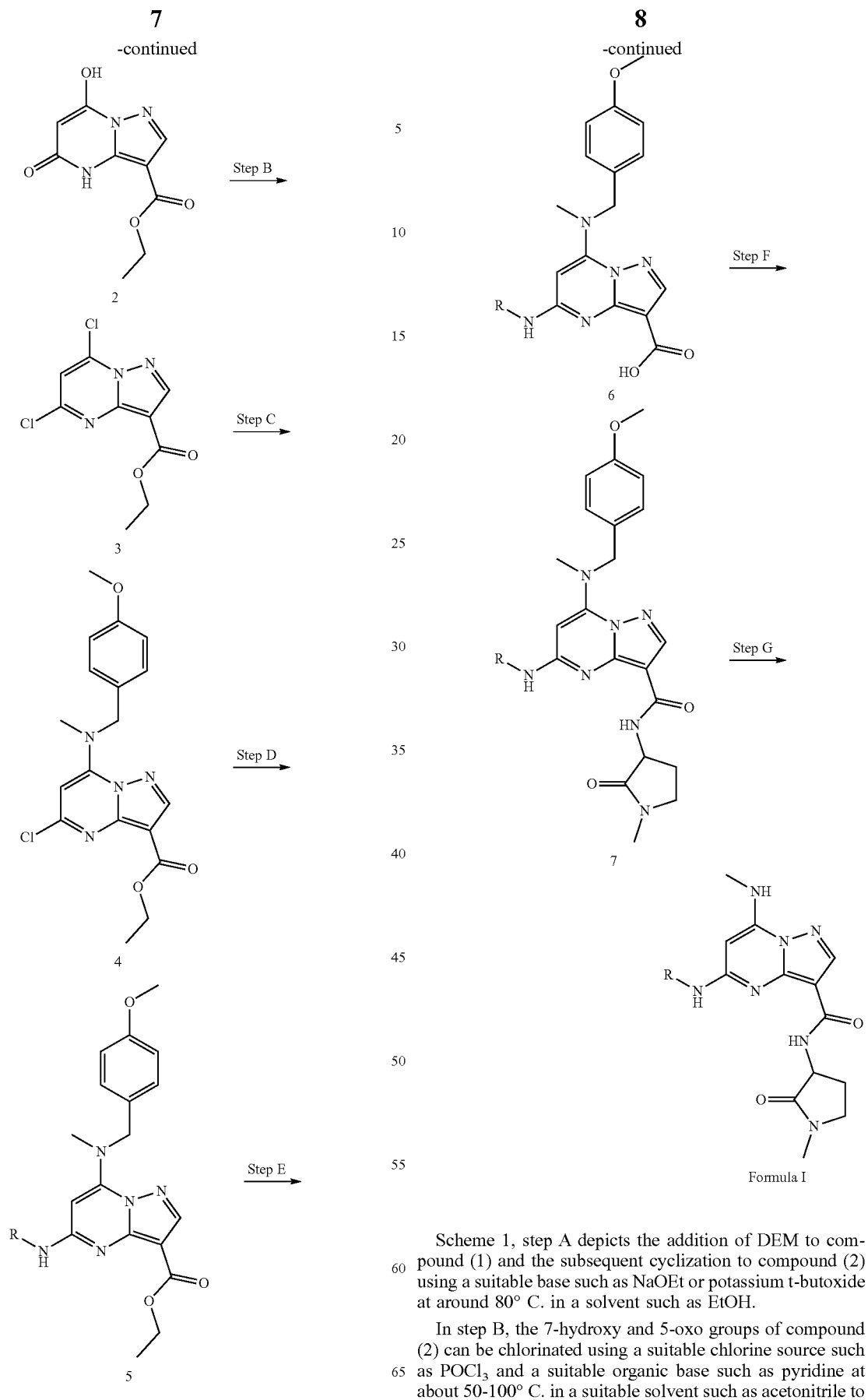

Scheme 1, step A depicts the addition of DEM to compound (1) and the subsequent cyclization to compound (2) using a suitable base such as NaOEt or potassium t-butoxide at around 80° C. in a solvent such as EtOH.

In step B, the 7-hydroxy and 5-oxo groups of compound (2) can be chlorinated using a suitable chlorine source such as POCl₃ and a suitable organic base such as pyridine at about 50-100° C. in a suitable solvent such as acetonitrile to give compound (3).

In step C, a selective nucleophilic aromatic substitution on the 7-chloro group of compound (3) can be performed under conditions well known in the art using a nucleophile such as 1-(4-methoxyphenyl)-N-methyl-methanamine and a suitable organic base such as DIEA in a suitable solvent such as 1,4-dioxane at ambient temperature to give compound (4).

In step D, a Buchwald coupling can be performed under conditions well known in the art on compound (4) with amines such as chroman-8-amine hydrochloride or 6-methylpyridin-2-amine to form compound (5) using a suitable catalyst and ligand combination such as Pd(OAc)$_2$ and BrettPhos, and a suitable base such as potassium carbonate in a solvent such as 1,4-dioxane with microwave heating at around 130° C.

Compound (5) can be treated with aqueous NaOH in solvents such as 1,4-dioxane and MeOH at about 50-80° C. to give compound (6) through basic hydrolysis of the ester as shown in step E.

In step F, an amide coupling can be performed between compound (6) and an amine such as (3R)-3-amino-1-methyl-pyrrolidin-2-one using a suitable organic base such as DIEA and a suitable coupling agent such as BOP in a suitable solvent such as DMF to give compound (7). One skilled in the art will recognize that there are several appropriate methods for amide formation resulting from the reaction of a carboxylic acid and an amine. For example, the reaction of the amine compound with an appropriate carboxylic acid in the presence of a coupling reagent with or without an organic base such as DIEA or TEA can provide a compound of step F. Coupling reagents include carbodiimides, such as DCC, DIC, EDCI or a carbonyldiimidazole such as CDI. Amide coupling additives, such as HOBt and HOAt can also be used to enhance the reaction. Additionally, uronium or phosphonium salts of non-nucleophilic anions, such as HBTU, HATU, PyBOP, and PyBrOP could be used in place of the more traditional coupling reagents. An additive such as DMAP may be used to enhance the reaction.

In step G, compound (7) is deprotected under standard conditions using a suitable acid such as TFA in a suitable solvent such as DCE at around 50° C. to give a compound of Formula I.

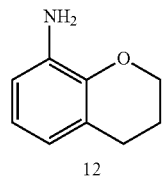

12

In scheme 2, step A, the formation of compound (9) is shown as a Suzuki-Miyaura cross coupling between compound (8) and potassium vinyltrifluoroborate using a suitable catalyst such as Pd(dppf)Cl$_2$ and a suitable base such as potassium carbonate in a suitable solvent system such as 1,4-dioxane and water at around 90° C.

In step B, a nucleophilic aromatic substitution is depicted under conditions well known in the art between compound (9) and allyl alcohol using an appropriate base such as potassium carbonate at around 60° C. to give compound (10).

A catalytic ring-closing metathesis of compound (10) is shown in step C using an appropriate catalyst such as Grubbs catalyst 2$^{nd}$ generation in an appropriate solvent such as DCM to give compound (11).

In step D, the palladium catalyzed nitro/alkene reduction of compound (11) is depicted under conditions well known in the art using an appropriate catalyst such as 10% Pd on carbon under a hydrogen atmosphere in a suitable solvent system such as MeOH and THF to give compound (12).

Scheme 2

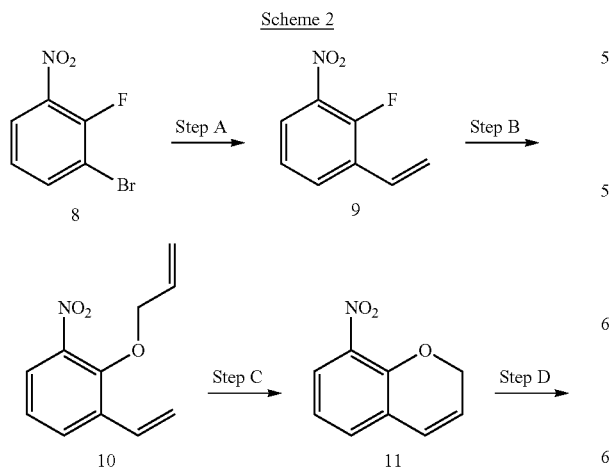

Scheme 3

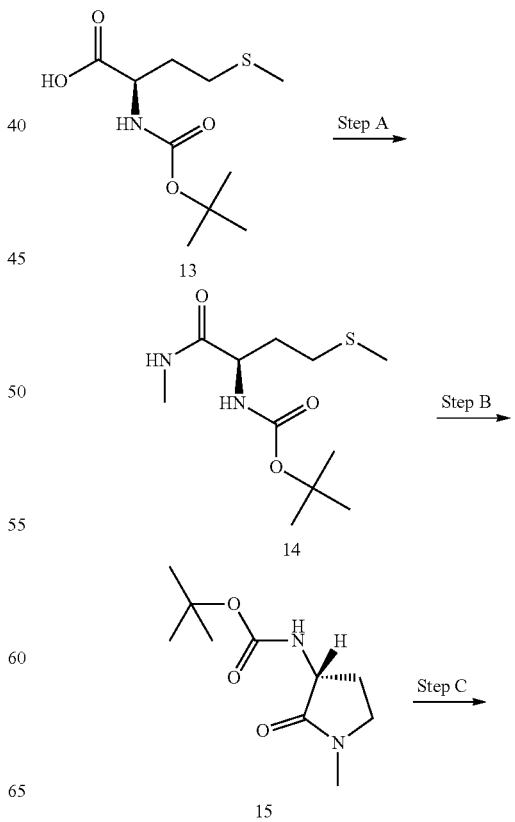

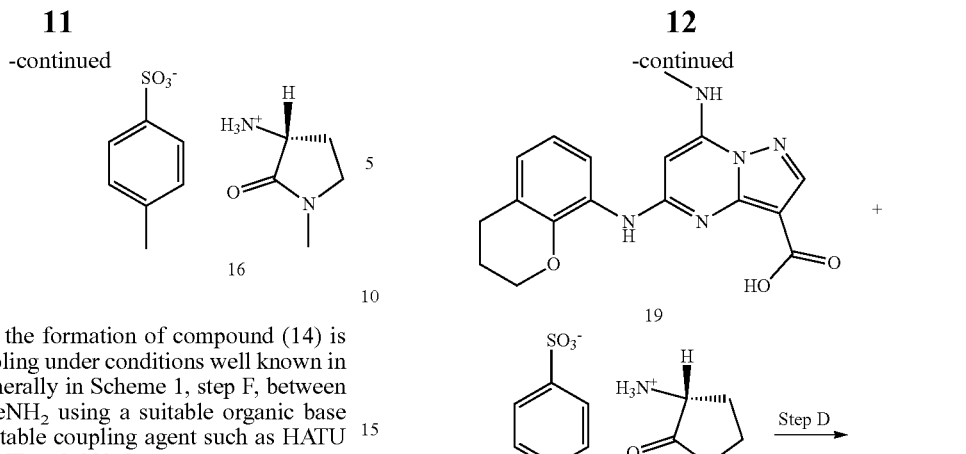

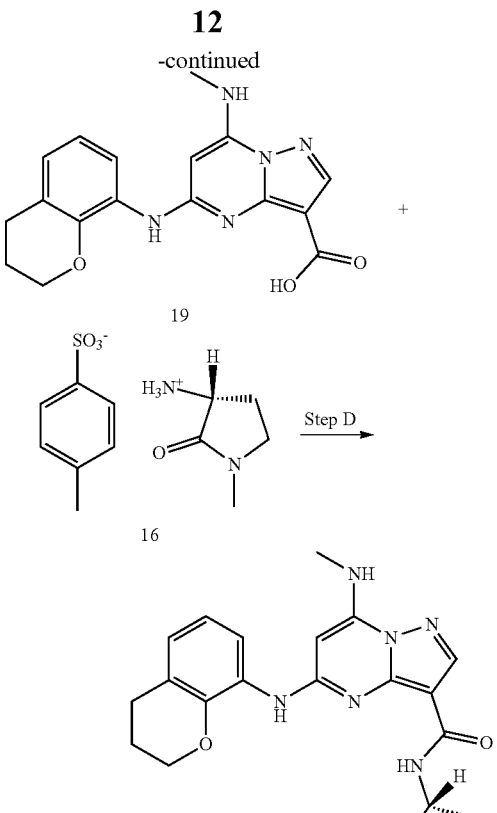

In scheme 3, step A, the formation of compound (14) is shown as an amide coupling under conditions well known in the art, as described generally in Scheme 1, step F, between compound (13) and MeNH$_2$ using a suitable organic base such as DIEA and a suitable coupling agent such as HATU in a solvent such as DMF at 0-22° C.

In step B, addition of MeI to compound (14) to form a dimethylsulfonium iodide salt followed by treatment with a suitable base such as LiHMDS in a suitable solvent such as THF at 0-22° C. can be used to give the cyclized compound (15).

In step C, compound (15) is deprotected under standard conditions using a suitable acid such as 4-methylbenzene-sulfonic acid in a suitable solvent such as acetonitrile at around 55° C., followed by addition of a solvent such as MTBE to precipitate compound (16).

Scheme 4

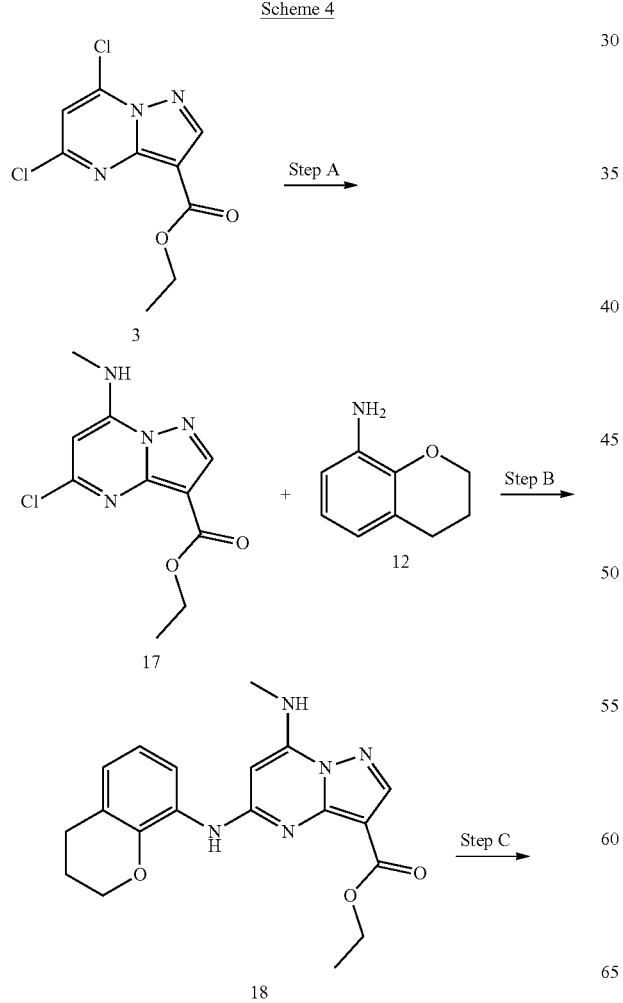

Compounds of Formula I, such as Formulas Ia(ii) and Ib(ii), can also be prepared as set forth in Scheme 4 utilizing the appropriate corresponding starting materials readily appreciated by one of ordinary skill in the art. More specifically, for example, in Scheme 4, step A, a selective nucleophilic aromatic substitution on the 7-chloro group of compound (3) can be performed under conditions well known in the art using an appropriate nucleophile such as MeNH$_2$ in a suitable solvent such as THF at ambient temperature to give compound (17).

In scheme 4, step A, a selective nucleophilic aromatic substitution on the 7-chloro group of compound (3) can be performed under conditions well known in the art using an appropriate nucleophile such as MeNH$_2$ in a suitable solvent such as THF at ambient temperature to give compound (17).

In step B, a Buchwald coupling can be performed on compound (17) with compound (12) to form compound (18) using a suitable catalyst and ligand system such as allylpalladium(II) chloride dimer and BINAP with a suitable base such as potassium acetate in an appropriate solvent system such as 1,4-dioxane and 2-methyl-2-butanol with heating at 125° C.

Compound (18) can be treated with a suitable base such as aqueous LiOH in a suitable solvent system such as MeOH and THF at reflux to give compound (19) through basic hydrolysis of the ester as shown in step C.

Step D depicts the formation of Formula Ia(ii) through an amide coupling under conditions well known in the art, as described generally in Scheme 1, step F, between compound

(19) and compound (16) using a suitable organic base such as DIEA and a suitable coupling agent such as BOP in a solvent such as DMF.

PREPARATION 1

Ethyl 7-hydroxy-5-oxo-4H-pyrazolo[1,5-a]pyrimidine-3-carboxylate

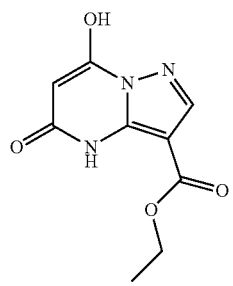 [SMILES: CCOC(=O)c1cnn2c(O)cc(=O)[nH]c12]

Scheme 1, step A: Ethyl 5-amino-1H-pyrazole-4-carboxylate (12.5 g, 80.6 mmol), and DEM (18.5 mL, 121 mmol) are dissolved in EtOH (90 mL). To this mixture is added NaOEt (21 mass % in EtOH, 45.1 mL, 121 mmol) and the reaction is stirred at 90° C. for 24 hours. After this time, the reaction is cooled to ambient temperature. The mixture is then made acidic with 5 N HCl aqueous solution and the resulting precipitate is filtered to give the title compound as a white solid (11.7 g, 65.1%). ES/MS m/z 224 (M+H).

Alternate Preparation 1

Scheme 1, step A: To a solution of ethyl 5-amino-1H-pyrazole-4-carboxylate (400 g, 2.58 mol) and DEM (584 mL, 3.87 mol) in EtOH (6.00 L) is added potassium t-butoxide (578 g, 5.16 mol) at 25° C. under nitrogen. The solution is stirred at 80° C. for 12 hours and then the reaction is cooled to 22° C. The reaction mixture is diluted with 0.1 N HCl (2 L) and the pH is adjusted to 3 with 5 N HCl. The mixture is filtered and the filter cake is washed with water (800 mL). The solid is dried under vacuum to constant weight to give the title compound as an off-white solid (460 g, 81%). ES/MS m/z 224 (M+H).

PREPARATION 2

Ethyl 5,7-dichloropyrazolo[1,5-a]pyrimidine-3-carboxylate

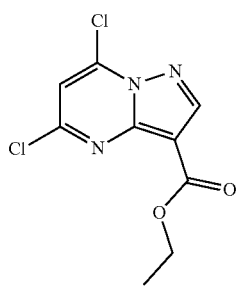 [SMILES: CCOC(=O)c1cnn2c(Cl)cc(Cl)nc12]

Scheme 1, step B: Ethyl 7-hydroxy-5-oxo-4H-pyrazolo[1,5-a]pyrimidine-3-carboxylate (11.7 g, 52.4 mmol) is suspended in acetonitrile (50 mL) and purged with nitrogen for 5 minutes. To this mixture is added POCl$_3$ (14.8 mL, 157 mmol) followed by pyridine (4.28 mL, 52.4 mmol) at 50° C. and then the reaction is stirred at 100° C. for 5 hours. After this time, the reaction is cooled to ambient temperature and poured into an ice/water mixture. This mixture is neutralized with saturated aqueous sodium bicarbonate solution and the resulting precipitate is filtered to give the title compound as a white solid (13 g, 95.3%). ES/MS m/z ($^{35}$Cl/$^{37}$Cl) 260/262 [M+H]$^+$.

Alternate Preparation 2

Scheme 1, step B: To a suspension of ethyl 7-hydroxy-5-oxo-4H-pyrazolo[1,5-a]pyrimidine-3-carboxylate (400 g, 1.79 mol) in acetonitrile (2 L), POCl$_3$ (416 mL, 4.48 mol) and pyridine (217 mL, 2.69 mol) are added drop-wise at 50° C. under nitrogen. The reaction is stirred at 80° C. for 12 hours. The reaction mixture is evaporated and the residue is poured into water (2 L). The reaction mixture is filtered and the solid is washed with water (800 mL). The solid is dried under vacuum to constant weight to give the title compound as an orange solid (360 g, 66%). ES/MS m/z ($^{35}$Cl/$^{37}$Cl) 260/262 [M+H]$^+$.

PREPARATION 3

Ethyl 5-chloro-7-[(4-methoxyphenyl)methyl-methyl-amino]pyrazolo[1,5-a]pyrimidine-3-carboxylate

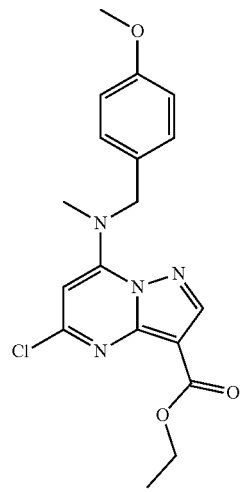 [SMILES: CCOC(=O)c1cnn2c(N(C)Cc3ccc(OC)cc3)cc(Cl)nc12]

Scheme 1, step C: Ethyl 5,7-dichloropyrazolo[1,5-a]pyrimidine-3-carboxylate (5 g, 19.2 mmol) is dissolved in 1,4-dioxane (40 mL). To this mixture is added 1-(4-methoxyphenyl)-N-methyl-methanamine (3.5 g, 20 mmol) followed by DIEA (6.7 mL, 38.4 mmol) and the reaction is stirred at ambient temperature for 2 hours. After this time, the reaction is quenched with water (100 mL) and extracted with EtOAc (3×100 mL). The combined organics are then dried over magnesium sulfate, filtered, and evaporated. This residue is purified via silica gel chromatography (0-70% EtOAc in hexanes) to give the title compound as a thick clear oil which solidifies to a white solid upon standing (3.55 g, 49.3%). ES/MS m/z ($^{35}$Cl/$^{37}$Cl) 375/377 [M+H]$^+$.

PREPARATION 3a

Ethyl 5-chloro-7-(methylamino)pyrazolo[1,5-a]pyrimidine-3-carboxylate

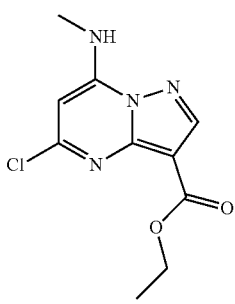 [SMILES: CCOC(=O)c1cnn2c(NC)cc(Cl)nc12]

Scheme 4, step A: Ethyl 5,7-dichloropyrazolo[1,5-a]pyrimidine-3-carboxylate (50.0 g, 192 mmol) is added to THF (250 mL) and the solution is cooled to 10° C. Then a solution of MeNH$_2$ (33% w/w in EtOH) (79 mL, 634 mmol) is added, keeping the temperature below 20° C. The reaction mixture is stirred and warmed to 22° C. and stirred for 4 hours. Then water (300 mL) is added and the mixture is stirred for an additional 1 hour.

The resulting solids are collected by filtration and washed with a THF/water mixture (2:3) (100 mL) and water (400 mL). The solid is then dried under vacuum (10 mbar/50° C.) to constant weight to give the title compound as pale brown solid (49.5 g, 90%). ES/MS m/z ($^{35}$Cl/$^{37}$Cl) 255/257 [M+H]$^+$.

PREPARATION 4

2-Fluoro-1-nitro-3-vinyl-benzene

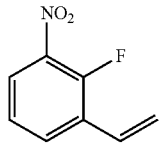

Scheme 2, step A: A flask is charged with potassium vinyltrifluoroborate (17 g, 120.6 mmol), potassium carbonate (40 g, 286.5 mmol), and Pd(dppf)Cl$_2$ (2 g, 2.7 mmol). The flask is evacuated and back filled with nitrogen three times. 1,4-Dioxane (450 mL), water (140 mL), and 1-bromo-2-fluoro-3-nitro-benzene (20 g, 90.1 mmol) are added. Again the flask is evacuated and back filled with nitrogen. The reaction mixture is heated to 90° C. for 3.5 hours and then allowed to cool to room temperature. The layers are separated and the organic layer is washed with saturated aqueous sodium chloride, dried over sodium sulfate, filtered, and evaporated. The residue is purified via silica gel chromatography (0-10% EtOAc in hexanes) to give the title compound as a light yellow oil (13.1 g, 84%). $^1$H NMR (d$_6$-DMSO) δ 8.09-8.03 (m, 2H), 7.44 (t, J=8.0 Hz, 1H), 6.91 (dd, J=11.2, 17.7 Hz, 1H), 6.08 (d, J=17.7 Hz, 1H), 5.62 (d, J=11.2 Hz, 1H).

PREPARATION 5

2-Allyloxy-1-nitro-3-vinyl-benzene

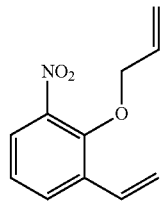

Scheme 2, step B: A mixture of allyl alcohol (18.8 g, 323 mmol), 2-fluoro-1-nitro-3-vinyl-benzene (12.2 g, 69.3 mmol), and potassium carbonate (31 g, 224 mmol) is heated to 60° C. for 16 hours and then allowed to cool to room temperature. The mixture is diluted with EtOAc (300 mL) and the solids are filtered off and discarded. The filtrate is evaporated and purified via silica gel chromatography (0-15% EtOAc in hexanes) to give the title compound as an oil (13.4 g, 88%). ES/MS m/z 206 (M+H).

PREPARATION 6

8-Nitro-2H-chromene

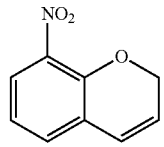

Scheme 2, step C: To 2-allyloxy-1-nitro-3-vinyl-benzene (13.4 g, 65.3 mmol) in DCM (500 mL) is added Grubbs catalyst 2$^{nd}$ generation (300 mg, 0.3 mmol). The flask is flushed with nitrogen and stirred at room temperature for 6 hours. The mixture is then evaporated and purified via silica gel chromatography (0-20% EtOAc in hexanes) to give the title compound as a waxy, yellow solid (10.6 g, 91%). ES/MS m/z 178 (M+H).

PREPARATION 7

Chroman-8-amine

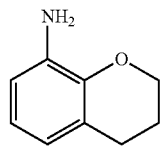 [SMILES: Nc1cccc2c1OCCC2]

Scheme 2, step D: A mixture of 8-nitro-2H-chromene (22.2 g, 125 mmol) and 10% Pd on carbon (600 mg, 0.53 mmol) in MeOH (350 mL) and THF (350 mL) is stirred under one atmosphere of hydrogen at room temperature. After 4 hours, a slurry of 10% Pd on carbon (450 mg, 0.4 mmol) in EtOAc (15 mL) is added and the mixture is stirred an additional 16 hours at room temperature under one atmosphere of hydrogen. The mixture is filtered and the filtrate is evaporated to give the title compound as an oil (17.6 g, 92%). ES/MS m/z 150 (M+H).

PREPARATION 8 tert-Butyl N-[(1R)-1-(methylcarbamoyl)-3-methyl-sulfanyl-propyl]carbamate

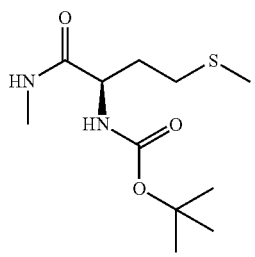 [SMILES: CNC(=O)[C@@H](CCSC)NC(=O)OC(C)(C)C]

Scheme 3, step A: A solution of (tert-butoxycarbonyl)-D-methionine (400 g, 1.6 mol), methyl amine hydrochloride (162.47 g, 2.4 mol), and DIEA (700 mL, 4.01 mol) in DMF (4 L) is cooled to 0° C. and HATU (732.1 g, 1.92 mol) is added. The reaction is warmed to ambient temperature. After 2 hours stirring, the solvent is evaporated. Then water (10 L) is added, and the aqueous solution is extracted with DCM (2×3 L). The organic layers are combined, washed with saturated aqueous sodium bicarbonate (3 L), dried over sodium sulfate, and evaporated. The resulting residue is purified by silica gel chromatography eluting with EtOAc in hexane to give the title compound as a white solid (368 g, 87%). ES/MS m/z 263 (M+H).

PREPARATION 9 tert-Butyl N-[(3R)-1-methyl-2-oxo-pyrrolidin-3-yl]carbamate

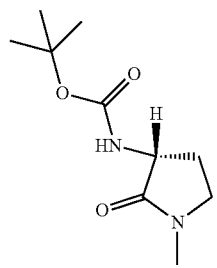

Scheme 3, step B: A mixture of tert-butyl N-[(1R)-1-(methylcarbamoyl)-3-methylsulfanyl-propyl]carbamate (368 g, 1.40 mol) and MeI (3.68 L, 59.11 mol) is stirred at ambient temperature for 18 hours. Then, the mixture is evaporated. A portion of the resulting crude dimethylsulfonium iodide salt (210 g, 0.52 mol) is dissolved in THF (4.7 L), cooled to 0° C. under a nitrogen atmosphere, and LiHMDS (1.00 M solution in THF, 1.16 L, 1.16 mol) is added dropwise. The reaction mixture is then warmed to ambient temperature. After 4 hours, water (2.4 L) is added and the solvent is evaporated to half volume. The mixture is extracted with DCM (2×3 L). The organics are combined and evaporated. The residue is purified by silica gel chromatography eluting with MeOH in DCM to give the title compound as white solid (50 g). ES/MS m/z 215 (M+H). Chiral HPLC: Rt (retention time)=9.13 minutes; LC Column: ChiralPAc IA OD 4.6×250 mm 5 μm; isocratic: 0.1% diethyl amine/hexanes/ethanol (85/15); Column Temp: 25° C.; Flow Rate: 1.0 mL/min. Optical rotation: $[\alpha]D^{20}=+53°$ (C=0.5, MeOH).

PREPARATION 10

(3R)-3-Amino-1-methyl-pyrrolidin-2-one; p-toluene Sulphonyl Salt

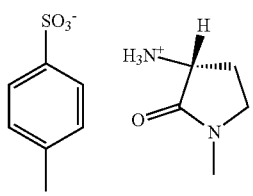

Scheme 3, step C: A mixture of tert-butyl N-[(3R)-1-methyl-2-oxo-pyrrolidin-3-yl]carbamate (46 g, 214.69 mmol) and 4-methylbenzenesulfonic acid (74.5 g, 433 mmol) in acetonitrile (500 mL) is heated at 55° C. and stirred for 4 hours. Then, MTBE (1 L) is added, and the mixture is cooled to 22° C. The resulting solid is collected by filtration, washed with additional MTBE, and dried under vacuum to constant weight to give the title compound as a white solid (60 g, 95%). ES/MS m/z 115 (M+H). Optical rotation: $[\alpha]_D^{20}=+31.3°$ (C=0.5, MeOH).

PREPARATION 11

Ethyl 5-(chroman-8-ylamino)-7-[(4-methoxyphenyl)methyl-methyl-amino]pyrazolo[1,5-a]pyrimidine-3-carboxylate

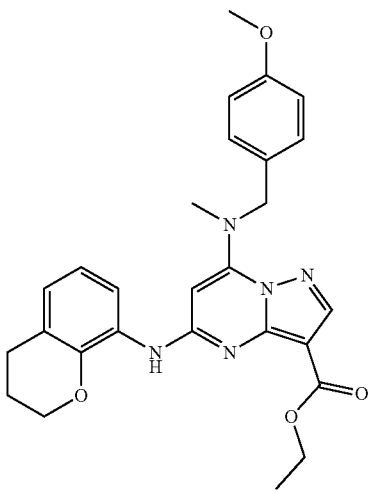 [SMILES: CCOC(=O)c1cnn2c(N(C)Cc3ccc(OC)cc3)cc(Nc3cccc4c3OCCC4)nc12]

Scheme 1, step D: To a flame dried microwave vial is added ethyl 5-chloro-7-[(4-methoxyphenyl)methyl-methyl-amino]pyrazolo[1,5-a]pyrimidine-3-carboxylate (400 mg, 1.1 mmol), chroman-8-amine hydrochloride (240 mg, 1.2 mmol), potassium carbonate (450 mg, 3.3 mmol), BrettPhos (60 mg, 0.1 mmol) and Pd(OAc)₂ (20 mg, 0.1 mmol). The vial is evacuated and back filled with nitrogen three times.

1,4-Dioxane (4.5 mL) is added and the vial is again flushed with nitrogen. The mixture is microwaved to 130° C. for 25 minutes, cooled to room temperature, diluted with MeOH (20 mL), filtered through diatomaceous earth, and evaporated. The resulting residue is purified via silica gel chromatography (0-40% EtOAc in hexanes) to give the title compound as an oil (232 mg, 42%). ES/MS m/z 488 (M+H).

The following compound is prepared in a manner essentially analogous to the method of Preparation 11.

rated aqueous sodium bicarbonate solution. The organic layer is washed with saturated aqueous sodium chloride, dried over sodium sulfate, filtered, and evaporated to a red semi-solid. To this residue is added DCM (85 mL) and the mixture is stirred for 5 minutes. The resulting solid is collected, washed with additional DCM, and dried under vacuum at room temperature to give a slightly peach colored material. The filtrate is concentrated to 60 mL total volume and stirred 5 minutes. The resulting solid is collected,

TABLE 1

| Prep. No. | Chemical name | Structure | Physical data |
|---|---|---|---|
| 12 | Ethyl 7-[(4-methoxyphenyl)methyl-methyl-amino]-5-[(6-methyl-2-pyridyl)amino]pyrazolo[1,5-a]pyrimidine-3-carboxylate | 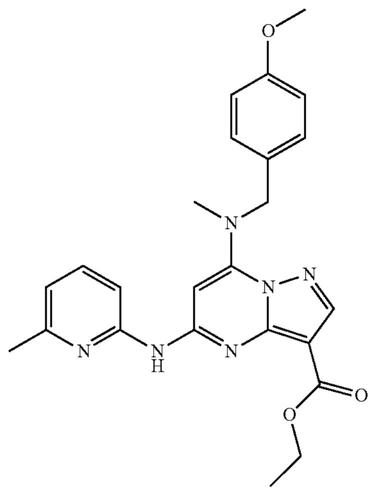 [SMILES: CCOC(=O)c1cnn2c(N(C)Cc3ccc(OC)cc3)cc(Nc3cccc(C)n3)nc12] | ES/MS m/z 447 (M + H). |

PREPARATION 11a

Ethyl 5-(chroman-8-ylamino)-7-(methylamino)pyrazolo[1,5-a]pyrimidine-3-carboxylate

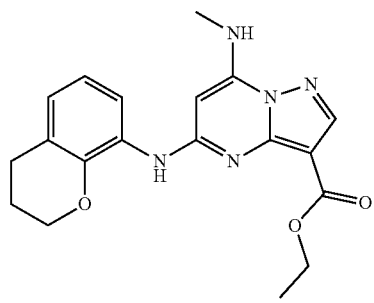 [SMILES: CCOC(=O)c1cnn2c(NC)cc(Nc3cccc4c3OCCC4)nc12]

Scheme 4, step B: A pressure flask is charged with ethyl 5-chloro-7-(methylamino)pyrazolo[1,5-a]pyrimidine-3-carboxylate (14 g, 55 mmol), BINAP (2.1 g, 3.3 mmol), allylpalladium(II) chloride dimer (620 mg, 1.7 mmol), and potassium acetate (10.8 g, 110 mmol) then flushed with nitrogen. A solution of chroman-8-amine (9 g, 60 mmol) in 1,4-dioxane (160 mL) that has been sparged for 10 minutes with nitrogen is added to the mixture followed by 2-methylbutan-2-ol (20 mL). The flask is flushed with nitrogen and heated at 125° C. After 2 hours, the mixture is cooled to room temperature and diluted with EtOAc (300 mL). The mixture is filtered through diatomaceous earth and evaporated. The residue is partitioned between EtOAc and saturated washed with additional DCM, combined with the previous crop of solids, and dried under vacuum to give 11.2 g of product. The remaining filtrate is purified via silica gel chromatography (0-50% EtOAc in hexanes) to give an additional 3.8 g of product. All collected solids are combined to give the title compound (15.0 g, 74%). ES/MS m/z 368.0 (M+H).

PREPARATION 13

5-(Chroman-8-ylamino)-7-[(4-methoxyphenyl)methyl-methyl-amino]pyrazolo[1,5-a]pyrimidine-3-carboxylic Acid

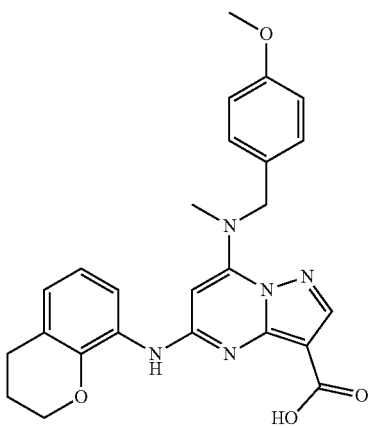 [SMILES: COc1ccc(CN(C)c2cc(Nc3cccc4c3OCCC4)nc3c(C(=O)O)cnn23)cc1]

Scheme 1, step E: A mixture of ethyl 5-(chroman-8-ylamino)-7-[(4-methoxyphenyl)methyl-methyl-amino]pyrazolo[1,5-a]pyrimidine-3-carboxylate (232 mg, 0.45 mmol), 5 N NaOH (1 mL, 5 mmol), MeOH (4 mL), and 1,4-dioxane (4 mL) is stirred at 50° C. After 16 hours, the reaction is cooled to room temperature and evaporated. To the residue is added DCM (25 mL), water (10 mL), and 5 N HCl (1 mL). After five minutes, the layers are separated. The organic layer is washed with saturated aqueous sodium chloride, dried over sodium sulfate, filtered, and evaporated to give the title compound as a faint peach solid (184 mg, 88%). ES/MS m/z 460 (M+H).

PREPARATION 13a 5-(Chroman-8-ylamino)-7-(methylamino)pyrazolo[1,5-a]pyrimidine-3-carboxylic Acid

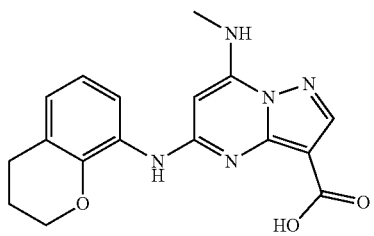 [SMILES: CNc1cc(Nc2cccc3c2OCCC3)nc2c(C(=O)O)cnn12]

Scheme 4, step C: To ethyl 5-(chroman-8-ylamino)-7-(methylamino)pyrazolo[1,5-a]pyrimidine-3-carboxylate (21.8 g, 59 mmol) in MeOH (200 mL) and THF (25 mL) is added a solution of LiOH (5.7 g, 240 mmol) in water (120 mL). The mixture is heated to reflux under nitrogen for one hour and then allowed to cool to room temperature. The pH is adjusted to ~2 by addition of 5 N HCl. Ice (125 g) is added to the mixture and the flask is placed in an ice water bath. After stirring for 30 minutes, the resulting solid is filtered, washed with ice cold water (75 mL), and dried under vacuum at room temperature to give the title compound as a light tan solid (18.2 g, 90%). ES/MS m/z 340.0 (M+H).

PREPARATION 14

7-[(4-Methoxyphenyl)methyl-methyl-amino]-5-[(6-methyl-2-pyridyl)amino]pyrazolo[1,5-a]pyrimidine-3-carboxylic Acid

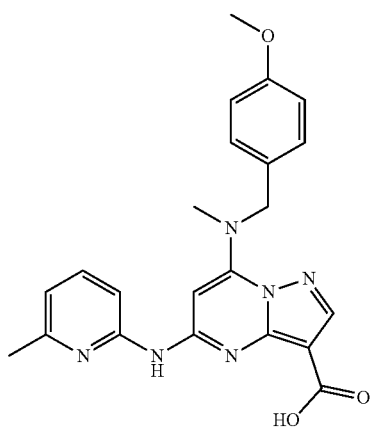 [SMILES: COc1ccc(CN(C)c2cc(Nc3cccc(C)n3)nc3c(C(=O)O)cnn23)cc1]

Scheme 1, step E: A mixture of ethyl 7-[(4-methoxyphenyl)methyl-methyl-amino]-5-[(6-methyl-2-pyridyl)amino]pyrazolo[1,5-a]pyrimidine-3-carboxylate (538 mg, 1.1 mmol), 5 N NaOH (0.8 mL, 4 mmol), MeOH (5 mL), and 1,4-dioxane (5 mL) is stirred at 80° C. After 4 hours, the mixture is cooled to room temperature and stirred overnight. The mixture is then diluted with water (50 mL) and the pH is adjusted to ~3 with 5 N HCl. The resulting solid is filtered and dried under vacuum at room temperature to give the title compound as a beige solid (493 mg, 99+%). ES/MS m/z 419 (M+H).

PREPARATION 15

5-(Chroman-8-ylamino)-7-[(4-methoxyphenyl)methyl-methyl-amino]-N-[(3R)-1-methyl-2-oxo-pyrrolidin-3-yl]pyrazolo[1,5-a]pyrimidine-3-carboxamide

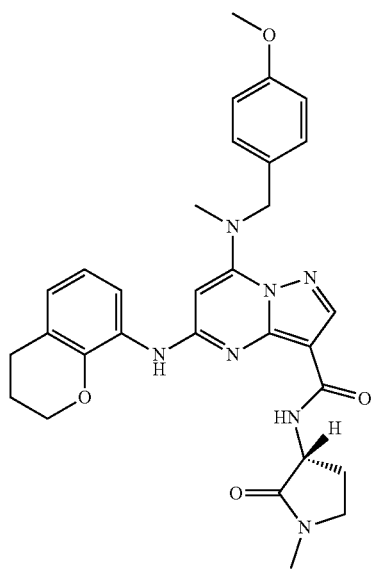 [SMILES: COc1ccc(CN(C)c2cc(Nc3cccc4c3OCCC4)nc3c(C(=O)N[C@@H]4CCN(C)C4=O)cnn23)cc1]

Scheme 1, step F: To a mixture of 5-(chroman-8-ylamino)-7-[(4-methoxyphenyl)methyl-methyl-amino]pyrazolo[1,5-a]pyrimidine-3-carboxylic acid (188 mg, 0.4 mmol), (3R)-3-amino-1-methyl-pyrrolidin-2-one (75 mg, 0.6 mmol) and DIEA (0.15 mL, 0.9 mmol) in DMF (4 mL) is added BOP (300 mg, 0.7 mmol). After stirring at room temperature for 30 minutes, the reaction mixture is partitioned between EtOAc and water. The organic layer is washed with saturated aqueous sodium chloride, dried over sodium sulfate, filtered, and evaporated. The resulting residue is purified via silica gel chromatography (0-40% MeOH in EtOAc) to give the title compound as a white solid (191 mg, 84%). ES/MS m/z 556 (M+H).

The following compound is prepared in a manner essentially analogous to the method of Preparation 15.

TABLE 2

| Prep. No. | Chemical name | Structure | Physical data |
|---|---|---|---|
| 16 | 7-[(4-Methoxyphenyl)methyl-methyl-amino]-N-[(3R)-1-methyl-2-oxo-pyrrolidin-3-yl]-5-[(6-methyl-2-pyridyl)amino]pyrazolo[1,5-a]pyrimidine-3-carboxamide | 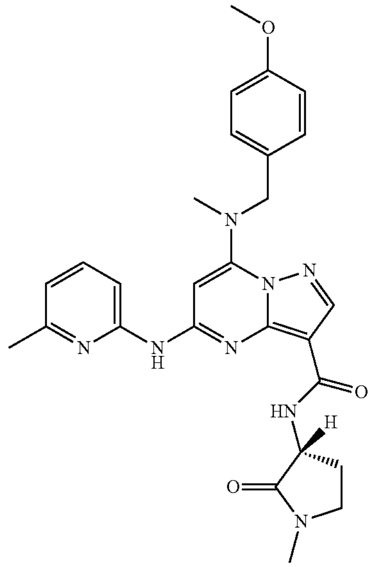 [SMILES: COc1ccc(CN(C)c2cc(Nc3cccc(C)n3)nc3c(C(=O)N[C@@H]4CCN(C)C4=O)cnn23)cc1] | ES/MS m/z 515 (M + H). |

PREPARATION 17

Preparation of the Tracer for the TYK2-JH2 Tracer Binding Assay (2E)-2-[(2E,4E)-5-[3-[6-[4-[4-[[5-[2-Methoxy-3-(1-methyl-1,2,4-triazol-3-yl)anilino]-6-(methylcarbamoyl)-1,2,4-triazin-3-yl]amino]pyrazol-1-yl]-1-piperidyl]-6-oxo-hexyl]-3-methyl-5-sulfonato-1-(3-sulfonatopropyl)indol-1-ium-2-yl]penta-2,4-dienylidene]-3,3-dimethyl-1-(3-sulfonatopropyl)indoline-5-sulfonate; triethylammonium 2-Methoxy-3-(1-methyl-1,2,4-triazol-3-yl)aniline (5.95 g, 29.1 mmol) is added to ethyl 5-chloro-3-methylsulfanyl-1,2,4-triazine-6-carboxylate (6.8 g, 29.0 mmol) in NMP (20 mL) and stirred at room temperature. After 90 minutes, diethyl ether (100 mL) is added and the mixture is stirred for 15 minutes. The resulting solid is filtered and washed with diethyl ether. The solid is partitioned between DCM and saturated aqueous sodium bicarbonate solution. The organic layer is further washed with saturated aqueous sodium chloride, dried over sodium sulfate, filtered, and evaporated to give ethyl 5-[2-methoxy-3-(1-methyl-1,2,4-triazol-3-yl)anilino]-3-methylsulfanyl-1,2,4-triazine-6-carboxylate as a faint yellow solid (10.12 g, 82%). ES/MS m/z 402.2 (M+H).

Ethyl 5-[2-methoxy-3-(1-methyl-1,2,4-triazol-3-yl)anilino]-3-methylsulfanyl-1,2,4-triazine-6-carboxylate (10.12 g, 23.7 mmol) is stirred in 2 M MeNH$_2$ in THF (75 mL, 150 mmol) at room temperature for 4 hours. Diethyl ether (100 mL) is added and the mixture is stirred for 15 minutes. The resulting solid is collected, washed with diethyl ether (50 mL), and dried under vacuum to give 5-[2-methoxy-3-(1-methyl-1,2,4-triazol-3-yl)anilino]-N-methyl-3-methylsulfanyl-1,2,4-triazine-6-carboxamide as a light yellow solid (8.03 g, 78%). ES/MS m/z 387.0 (M+H).

m-Chloroperoxybenzoic acid (703 mg, 3.14 mmol) is added to a suspension of 5-[2-methoxy-3-(1-methyl-1,2,4-triazol-3-yl)anilino]-N-methyl-3-methylsulfanyl-1,2,4-triazine-6-carboxamide (500 mg, 1.26 mmol) in DMF (12.5 mL) at 0° C. and allowed to warm to room temperature. After 30 minutes, tert-butyl 4-(4-aminopyrazol-1-yl)piperidine-1-carboxylate (520 mg, 1.89 mmol) is added and the mixture is stirred at room temperature. After 24 hours, the mixture is partitioned between DCM and saturated aqueous sodium bicarbonate. The organic layer is dried over magnesium sulfate, filtered, and evaporated. The resulting solid is triturated several times with diethyl ether and dried under vacuum to give tert-butyl 4-[4-[[5-[2-methoxy-3-(1-methyl-1,2,4-triazol-3-yl)anilino]-6-(methylcarbamoyl)-1,2,4-triazin-3-yl]amino]pyrazol-1-yl]piperidine-1-carboxylate as an 86% pure yellow solid (720 mg, 81%). ES/MS m/z 605.2 (M+H).

4 N HCl in dioxane (2.5 mL, 10 mmol) is added to a suspension of tert-butyl 4-[4-[[5-[2-methoxy-3-(1-methyl-1,2,4-triazol-3-yl)anilino]-6-(methylcarbamoyl)-1,2,4-triazin-3-yl]amino]pyrazol-1-yl]piperidine-1-carboxylate (720 mg, 1.0 mmol) in MeOH (5 mL) and stirred at room temperature. After 72 hours, the mixture is evaporated. The resulting material is partitioned between DCM (100 mL) and water (20 mL). The pH of the aqueous layer is adjusted to >8 by addition of 1N NaOH and extracted with 3:1 chloroform/isopropanol. The organic layers are combined, dried over magnesium sulfate, filtered, and evaporated. The resulting solid is triturated with diethyl ether and then dried under vacuum to give 5-[2-methoxy-3-(1-methyl-1,2,4-triazol-3-yl)anilino]-N-methyl-3-[[1-(4-piperidyl)pyrazol-4-yl]amino]-1,2,4-triazine-6-carboxamide as an 86% pure yellow solid (585 mg, 97%). ES/MS m/z 505.0 (M+H).

A solution of (2E)-2-[(2E,4E)-5-[3-[6-(2,5-dioxopyrrolidin-1-yl)oxy-6-oxo-hexyl]-3-methyl-5-sulfonato-1-(3-sulfonatopropyl)indol-1-ium-2-yl]penta-2,4-dienylidene]-3,3-dimethyl-1-(3-sulfonatopropyl)indoline-5-sulfonate triethylammonium (10 mg, 0.008 mmol) in DMSO (1 mL) is added to a solution of 5-[2-methoxy-3-(1-methyl-1,2,4-triazol-3-yl)anilino]-N-methyl-3-[[1-(4-piperidyl)pyrazol-4-yl]amino]-1,2,4-triazine-6-carboxamide (4.5 mg, 0.008 mmol) and TEA (0.002 mL, 0.014 mmol) in DMSO (1 mL). The reaction vial is wrapped in aluminum foil to protect from light and stirred at room temperature overnight. The resulting residue is purified by prep HPLC (Kinetix EVO C18 30 mm×100 mm, 5um) eluting with 0 to 20% acetonitrile in water to give the title compound as a bright blue solid (8.5 mg, 65%). ES/MS m/z 673.4 (M+H).

Example 1

5-(Chroman-8-ylamino)-7-(methylamino)-N-[(3R)-1-methyl-2-oxo-pyrrolidin-3-yl]pyrazolo[1,5-a]pyrimidine-3-carboxamide

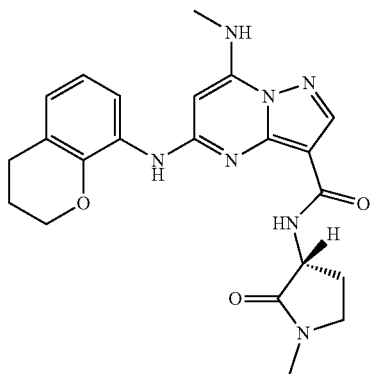 [SMILES: CNc1cc(Nc2cccc3c2OCCC3)nc2c(C(=O)N[C@@H]3CCN(C)C3=O)cnn12]

Scheme 1, step G: To 5-(chroman-8-ylamino)-7-[(4-methoxyphenyl)methyl-methyl-amino]-N-[(3R)-1-methyl-2-oxo-pyrrolidin-3-yl]pyrazolo[1,5-a]pyrimidine-3-carboxamide (191 mg, 0.3 mmol) in DCE (3 mL) is added TFA (1.5 mL, 20 mmol). The mixture is heated to 50° C. for 4 hours, cooled to room temperature, and stirred overnight. The mixture is evaporated and partitioned between DCM and saturated sodium bicarbonate solution. The organic layer is washed with saturated aqueous sodium chloride, dried over sodium sulfate, filtered, and evaporated. The resulting residue is purified via high pH LC/MS to give the title compound as a white solid (31 mg, 21%). ES/MS m/z 436 (M+H).

Alternate Procedure for Preparation of Example 1

5-(Chroman-8-ylamino)-7-(methylamino)-N-[(3R)-1-methyl-2-oxo-pyrrolidin-3-yl]pyrazolo[1,5-a]pyrimidine-3-carboxamide Scheme 4, step D: To (3R)-3-amino-1-methyl-pyrrolidin-2-one 4-methylbenzenesulfonic acid salt (15 g, 51 mmol) in DMF (200 mL) is added DIEA (29 mL, 166 mmol). After stirring for 5 minutes, 5-(chroman-8-ylamino)-7-(methylamino)pyrazolo[1,5-a]pyrimidine-3-carboxylic acid (14 g, 41 mmol) is added followed by BOP (24 g, 53 mmol). After stirring 30 minutes, water (200 mL) is added followed by saturated sodium bicarbonate solution (400 mL) and the flask is cooled in an ice water bath. After stirring for 90 minutes, the resulting solids are filtered, washed with additional water, and dried under vacuum. The solids are dissolved in a 3:1 mixture of chloroform:isopropanol, washed with 2 N NaOH and saturated aqueous sodium chloride, dried over sodium sulfate, filtered, and evaporated. The material is purified via silica gel chromatography (0-8% MeOH in DCM) to give the title compound as an off-white solid (6.7 g). ES/MS m/z 436.0 (M+H).

Example 2

7-(Methylamino)-N-[(3R)-1-methyl-2-oxo-pyrrolidin-3-yl]-5-[(6-methyl-2-pyridyl)amino]pyrazolo[1,5-a]pyrimidine-3-carboxamide

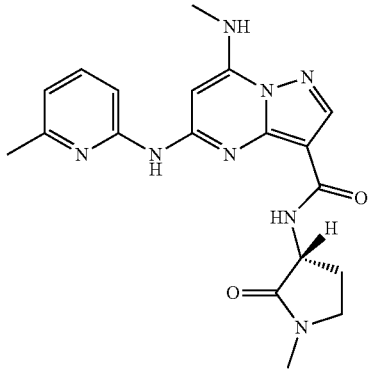 [SMILES: CNc1cc(Nc2cccc(C)n2)nc2c(C(=O)N[C@@H]3CCN(C)C3=O)cnn12]

Scheme 1, step G: TFA (1 mL, 13.2 mmol) is added to 7-[(4-methoxyphenyl)methyl-methyl-amino]-N-[(3R)-1-methyl-2-oxo-pyrrolidin-3-yl]-5-[(6-methyl-2-pyridyl)amino]pyrazolo[1,5-a]pyrimidine-3-carboxamide (93 mg, 0.18 mmol) in DCE (2 mL) and the mixture is heated to 50° C. After 1 hour, the mixture is cooled to room temperature and evaporated. To the residue is added DCM and saturated sodium bicarbonate solution. The mixture is stirred for 10 minutes and the resulting solid is collected. The solid is washed with water and diethyl ether then dried under vacuum to give the title compound as a beige solid (72 mg). ES/MS m/z 395 (M+H).

TYK2-JH2 Tracer Binding Assay

The pseudokinase domain (JH2) of human JAK (Janus family of cytoplasmic tyrosine kinases) family tyrosine kinase 2 (TYK2) (Genbank NP_003322) with an N-terminal His6 tag is expressed in baculovirus and purified by HisPur Ni-NTA affinity and Superdex 200 size-exclusion chromatography. The compound prepared in Preparation 17, a conjugate of Alexa Fluor 647 dye (Thermo Fisher Scientific) and a suitable TYK2 JH2 binder, is referred to herein as "the Tracer". A 3 fold, 10 point serial dilution of compound, Example 1 and Example 2, are prepared in 100% DMSO and 50 nL/well transferred to a Proxiplate-384F white plate (PerkinElmer 6008280) using acoustic liquid handling. Control wells used to determine percent inhibition contained 100% DMSO (50 nL) and either assay buffer containing the Tracer (2.00 nM final concentration) (min, low FRET) or diluted TYK2-JH2 enzyme (0.200 nM final concentration) and the Tracer (2.00 nM final concentration) (max, high FRET).

5.0 μL of His-tagged TYK2-JH2 (0.402 nM) and LanthaScreen Eu-anti-HIS Ab (4.02 nM, LifeTech, PV5597) in assay buffer (50 mM HEPES pH 7.5, 10 mM magnesium chloride, 1 mM ethylene glycol-bis(β-aminoethyl ether)-N,N,N',N'-tetraacetic acid, 0.01% Brij-35 and Milli-Q) water is added to the Proxiplate-384 plate containing the 50 nL of diluted compound and control wells. 5.0 μL of the Tracer (2.00 nM final concentration) in assay buffer is added to the plate and allowed to equilibrate for 30 minutes at room temperature. After 30 minutes, the plate is counted on a PerkinElmer Envision with the following settings: Excitation (340 nm), Tracer Emission (665 nm) and LanthaScreen Eu-anti-His Antibody Emission (615 nm). The ratio of Tracer Emission (665 nm) over LanthaScreen Eu-anti-His Antibody Emission (615 nm) is determined. Percent inhibition of ratio at each inhibitor concentration is calculated using the max and min control wells and fit to the four parameter nonlinear logistic equation in GeneData Screener® to give an $IC_{50}$ for the compound of Example 1 of <0.000254 μM (n=2) and for the compound of Example 2 of <0.000254 μM (n=1). This result demonstrates that the compounds of Example 1 and Example 2 bind to the TYK2-JH2 pseudo kinase domain in vitro.

Inhibition of IFNα Signaling Through pSTAT1 in TF1 Cells

TF1 cells (ATCC, CL-2003) are grown in RPMI 1640 (GIBCO) supplemented with 10% dialyzed FBS, 0.1 mg/mL Ampicillin and 2 ng/mL granulocyte macrophage colony stimulating factor. TF1 cells (100 K per well) are seeded in a 96-well poly-D-lysine coated plates in serum-free DMEM and incubated overnight at 37° C. under 5% $CO_2$. Example 1 is serially diluted in DMSO, added to the cells, and incubated at 37° C. for 1 hr. Cells are then stimulated with 10 ng/mL IFNα2 at 37° C. for 20 minutes. After removing the medium, the cells are lysed in buffer containing Halt protease and phosphatase inhibitor cocktail (Thermo Scientific #78441) at room temperature for 30 minutes. The amount of p-Stat1 (Tyr701) is quantified as light emission at 615 nm using the AlphaLISA SureFire Ultra p-Stat1 (Tyr701) assay kit (Perkin Elmer #ALSU-PST1-A50K) following the vendor's recommended protocol. Percent inhibition at each inhibitor concentration is calculated and fit to the four parameter nonlinear logistic equation using Genedata Screener® to give an $IC_{50}$ for the compound of Example 1 of 0.007 μM (0.002 μM, n=4) and for the compound of Example 2 of 0.100 μM (0.014 μM, n=4) expressed as GeoMetric means with the standard error of the mean (SEM). This result demonstrates that the compounds of Example 1 and Example 2 are inhibitors of IFNα signaling through pSTAT1 in TF1 cells.

IL23 pSTAT3 AlphaLISA Assay

IL2-dependent Kit225 cells (University of Texas MD Anderson Cancer Center) expressing endogenous IL23 receptors are stably transduced with the Lenti STAT3 Reporter linked to firefly luciferase (SABiosciences CLS-6028L). These cells are used to monitor TYK2 activity by quantifying gene expression caused by STAT3 phosporylation following induction by IL23 in the presence of IL2 using AlphaLISA technology (TGR Biosciences ALSU-TST3-A50K). The cells are grown in RPMI 1640 (Gibco 22400) supplemented with 10% FBS (Invitrogen 10082), 1× Pen/Strep (Gibco 15140-122), 200 ng/ml Puromycin (Sigma P9620), and fresh 10 ng/ml recombinant human IL2 (R&D Systems 202-IL-50).

For assay preparation, cells are dispensed into Biocoat black poly-d-lysine coated clear bottom 384-well plates (Becton Dickinson Bio-Coat 35-4640) in DMEM (Sigma D5796) at 300,000 cells/well and allowed to incubate overnight at 37° C. Compounds solubilized in DMSO are serially diluted 1:3 to produce a 10-point concentration response curve (final DMSO=0.1%). Cells are pre-incubated with Example 1 for 1 hour at 37° C., then stimulated with IL23 (25 ng/mL final) for 30 minutes. After centrifugation at 2000 rpm for 10 minutes, cell pellets are lysed with a mixture of 1:1 lysis buffer (TGR Biosciences) and Halt Protease & Phosphatase inhibitor cocktail (Thermo Scientific 1861281) for 30 minutes. The AlphaLISA reaction is performed following the vendor's recommended protocol, and the luciferase levels are measured using an Envision plate reader (Perkin Elmer). The relative $IC_{50}$ is calculated using a 4-parameter nonlinear logistic equation (GeneData Screener 13.0.5) to give an $IC_{50}$ for the compound of Example 1 of 0.007 μM (0.001 μM, n=3) and for the compound of Example 2 of 0.066 μM (±0.014 μM, n=3) expressed as GeoMetric means with the standard error of the mean (SEM). This result demonstrates that the compounds of Example 1 and Example 2 are inhibitors of IL-23 signaling in a cell-based assay.

We claim:

1. A compound of the formula:

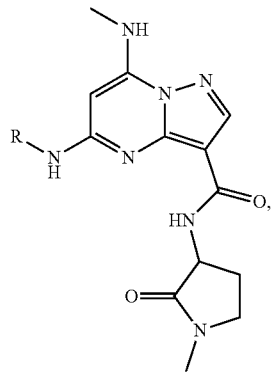

wherein R is

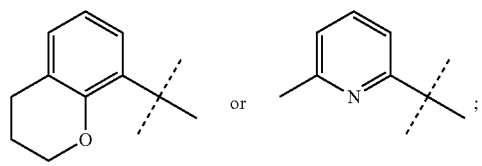

or a pharmaceutically acceptable salt thereof.

2. The compound according to claim 1 wherein R is

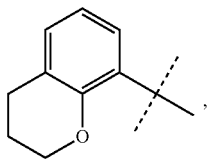

or a pharmaceutically acceptable salt thereof.

3. The compound according to claim 1 wherein R is

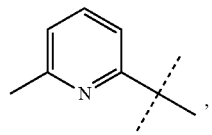

or a pharmaceutically acceptable salt thereof.

4. The compound according to claim 1 of the formula:

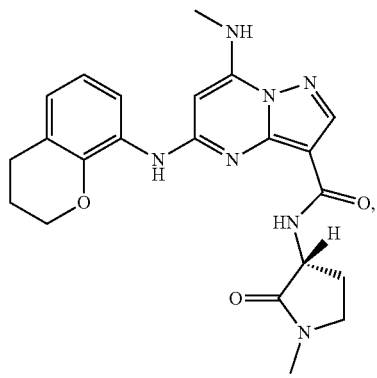 [SMILES: CNc1cc(Nc2cccc3c2OCCC3)nc2c(C(=O)N[C@@H]3CCN(C)C3=O)cnn12]

or a pharmaceutically acceptable salt thereof.

5. The compound according to claim 4 of the formula:

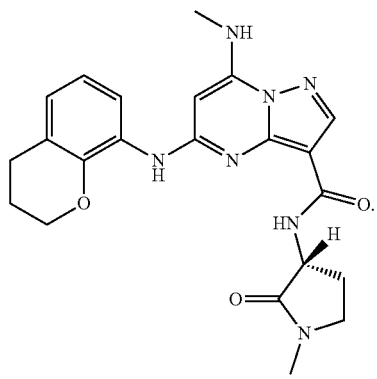 [SMILES: CNc1cc(Nc2cccc3c2OCCC3)nc2c(C(=O)N[C@@H]3CCN(C)C3=O)cnn12]

6. The compound according to claim 1 of the formula:

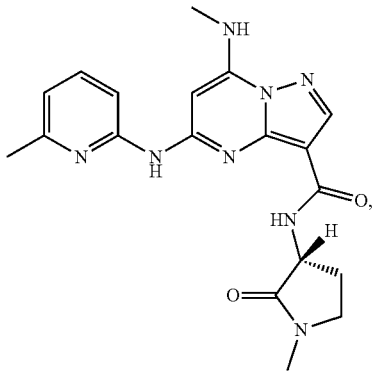 [SMILES: CNc1cc(Nc2cccc(C)n2)nc2c(C(=O)N[C@@H]3CCN(C)C3=O)cnn12]

or a pharmaceutically acceptable salt thereof.

7. The compound according to claim 6 of the formula:

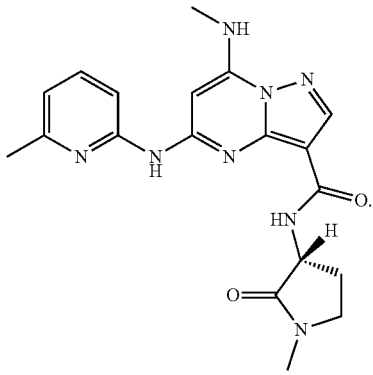 [SMILES: CNc1cc(Nc2cccc(C)n2)nc2c(C(=O)N[C@@H]3CCN(C)C3=O)cnn12]

8. A method of treating psoriasis in a patient, comprising administering to a patient in need of such treatment an effective amount of a compound according to claim 1, or a pharmaceutically acceptable salt thereof.

9. A method of treating systemic lupus erythematosus in a patient, comprising administering to a patient in need of such treatment an effective amount of a compound according to claim 1, or a pharmaceutically acceptable salt thereof.

10. A pharmaceutical composition, comprising a compound or a pharmaceutically acceptable salt thereof, according to claim 1 with one or more pharmaceutically acceptable carriers, diluents, or excipients.

11. A process for preparing a pharmaceutical composition, comprising admixing a compound or a pharmaceutically acceptable salt thereof according to claim 1 with one or more pharmaceutically acceptable carriers, diluents, or excipients.

* * * * *